United States Patent
Hietanen et al.

(10) Patent No.: US 11,096,817 B2
(45) Date of Patent: Aug. 24, 2021

(54) THERAPY TAPE TO AID PATIENT RECOVERY

(71) Applicant: 6D Tape Inc., Sipoo (FI)

(72) Inventors: Sari Johanna Hietanen, Nummela (FI); Leo Tapani Taskinen, Espoo (FI)

(73) Assignee: 6D Tape Inc, Sipoo (FI)

( * ) Notice: Subject to any disclaimer, the term of this patent is extended or adjusted under 35 U.S.C. 154(b) by 266 days.

(21) Appl. No.: 15/297,410

(22) Filed: Oct. 19, 2016

(65) Prior Publication Data
US 2018/0104087 A1  Apr. 19, 2018

(51) Int. Cl.
*A61F 5/40* (2006.01)
*A61H 7/00* (2006.01)
(Continued)

(52) U.S. Cl.
CPC .............. *A61F 5/40* (2013.01); *A61F 13/023* (2013.01); *A61F 13/0223* (2013.01);
(Continued)

(58) Field of Classification Search
CPC ............ A61B 17/085; A61B 17/08–10; A61B 17/0281; A61F 5/40; A61F 2013/00089–2013/00357; A61F 13/00–00085; A61F 13/02–0273; A61F 2013/00919; A61H 7/00; A61H 7/001; A61H 7/007; A61H 7/008; A61H 11/00–02; A61H 23/02; A61H 2201/50; A61H 2201/5007; A61H 2201/501;
(Continued)

(56) References Cited

U.S. PATENT DOCUMENTS 2,349,709 A  5/1944 Evans
2,472,009 A *  5/1949 Gardner ................. A61B 17/08
606/215
(Continued)

FOREIGN PATENT DOCUMENTS

CA  2578827 A1  5/1999
DE  102005009635 A1  9/2006
(Continued)

OTHER PUBLICATIONS

San Diego Plastics, Polyurethane, http://www.sdplastics.com/polyuret.html (Year: 1996).*
(Continued)

*Primary Examiner* — Alireza Nia
*Assistant Examiner* — Michelle J Lee
(74) *Attorney, Agent, or Firm* — Alston & Bird LLP (57) ABSTRACT

Various embodiments are directed to a therapy tape configured to enable a tensile force to be applied to one or more surfaces (e.g., a patient's skin). In various embodiments, the therapy tape may comprise a backing layer having a top surface and a bottom surface. An adhesive layer configured to secure the therapy tape to a surface may be secured relative to the bottom surface of the backing layer. Moreover, one or more handles may be secured to the top side of the backing layer. The one or more handles may be configured to enable a tensile force to be applied to the therapy tape and the surface to lift a portion of the surface while maintaining adherence between the therapy tape and the surface.

12 Claims, 6 Drawing Sheets

(51) Int. Cl.
*A61H 23/02* (2006.01)
*A61H 11/00* (2006.01)
*A61F 13/02* (2006.01)
*C09J 7/35* (2018.01)
*A61F 13/00* (2006.01)

(52) U.S. Cl.
CPC ............ *A61H 7/001* (2013.01); *A61H 7/008* (2013.01); *A61H 11/00* (2013.01); *A61H 23/02* (2013.01); *C09J 7/35* (2018.01); *A61F 2013/00919* (2013.01); *A61H 2201/5012* (2013.01); *A61H 2201/5097* (2013.01)

(58) Field of Classification Search
CPC ..... A61H 2201/5012; A61H 2201/5097; C09J 7/00; C09J 7/20; C09J 7/30; C09J 7/35
See application file for complete search history.

(56) References Cited

U.S. PATENT DOCUMENTS

| | | | |
|---|---|---|---|
| 3,669,106 A * | 6/1972 | Schrading | A61B 46/00 128/853 |
| 4,008,721 A | 2/1977 | Burton | |
| 4,374,520 A | 2/1983 | Frederic et al. | |
| 4,539,990 A * | 9/1985 | Stivala | A61B 17/085 606/215 |
| 4,650,705 A * | 3/1987 | Ghodsian | A61B 17/0281 428/40.6 |
| 4,664,103 A * | 5/1987 | Martin | A61B 46/00 128/852 |
| 4,925,453 A * | 5/1990 | Kannankeril | A61F 13/36 128/917 |
| 5,582,585 A * | 12/1996 | Nash-Morgan | A45D 44/22 428/343 |
| 5,861,348 A | 1/1999 | Kase | |
| 6,297,422 B1 * | 10/2001 | Hansen | A61F 13/023 602/54 |
| D607,114 S | 12/2009 | Arbesman et al. | |
| D608,894 S | 1/2010 | Arbesman et al. | |
| D608,896 S | 1/2010 | Arbesman et al. | |
| D612,507 S | 3/2010 | Arbesman et al. | |
| D616,553 S | 5/2010 | Arbesman et al. | |
| D621,053 S | 8/2010 | Kase | |
| D621,054 S | 8/2010 | Kase | |
| D625,422 S | 10/2010 | Arbesman et al. | |
| 7,902,420 B2 | 3/2011 | Kase | |
| D639,962 S | 6/2011 | Kase | |
| D639,964 S | 6/2011 | Kase | |
| D641,083 S | 7/2011 | Kase | |
| D649,255 S | 11/2011 | Kase | |
| D674,098 S | 1/2013 | Nichols | |
| 8,604,266 B2 * | 12/2013 | Spinelli | A61F 13/0226 424/446 |
| 8,742,196 B2 | 6/2014 | Arbesman et al. | |
| 9,119,620 B2 * | 9/2015 | Peterson | A61B 17/085 |
| D743,566 S | 11/2015 | Arbesman | |
| 9,615,975 B2 * | 4/2017 | Rastegar | A61F 13/0233 |
| 2002/0193724 A1 * | 12/2002 | Stebbings | A61F 13/0246 602/54 |
| 2003/0045825 A1 * | 3/2003 | Etheredge | A61F 13/0206 602/45 |
| 2008/0154169 A1 | 6/2008 | Kase | |
| 2008/0281245 A1 | 11/2008 | Effing et al. | |
| 2010/0121286 A1 * | 5/2010 | Locke | A61B 17/085 604/319 |
| 2010/0137775 A1 | 6/2010 | Hu et al. | |
| 2010/0228304 A1 | 9/2010 | Kriksunov et al. | |
| 2010/0298747 A1 * | 11/2010 | Quinn | A61F 13/023 602/1 |
| 2012/0221044 A1 * | 8/2012 | Archibald | A61B 17/08 606/214 |
| 2012/0232448 A1 | 9/2012 | Wüst | |
| 2014/0128819 A1 * | 5/2014 | Eaves | A61B 17/085 604/264 |
| 2014/0243589 A1 | 8/2014 | Rowan | |
| 2016/0106595 A1 | 4/2016 | Arbesman et al. | |
| 2016/0262943 A1 | 9/2016 | Arbesman et al. | |
| 2018/0049833 A1 * | 2/2018 | Shelton, IV | A61B 34/35 |

FOREIGN PATENT DOCUMENTS

| | | |
|---|---|---|
| EP | 0161865 A2 | 11/1985 |
| EP | 1716829 A1 | 11/2006 |
| JP | S60-55405 U | 4/1985 |
| JP | H09-70442 A | 3/1997 |
| JP | 11-192312 A | 7/1999 |
| WO | WO 2003/017899 A1 | 3/2003 |
| WO | WO 2008/048350 A2 | 4/2008 |
| WO | WO 2012/170744 A2 | 12/2012 |
| WO | WO 2013/142018 A1 | 9/2013 |

OTHER PUBLICATIONS

International Searching Authority, International Search Report and Written Opinion for International Application No. PCT/EP2017/076547, Jan. 29, 2018, 16 pages, European Patent Office, Netherlands.

Japan Patent Office, Office Action for Application No. 2019-542784, dated Aug. 12, 2020, 8 pages, Japan.

* cited by examiner

THERAPY TAPE TO AID PATIENT RECOVERY

BACKGROUND

In general, therapeutic treatment to aid patients' recovery from bodily injuries (e.g., strained, damaged, or weakened muscles, torn and/or strained ligaments, bruising, and/or the like) and/or medical procedures (e.g., surgical procedures, such as joint replacement), and/or to minimize patient discomfort from disabilities and/or other conditions (e.g., Fibromyalgia, Multiple Sclerosis (MS), and/or the like) involves professional-guided treatment sessions (e.g., under the guidance of a physician, physical therapist, and/or the like) and/or patient-guided treatment sessions (e.g., self-guided exercises) that may be prescribed by the overseeing professional. While the professional-guided treatment sessions may involve an exercise portion in which the patient performs exercises similar to those included in the patient-guided treatment sessions, professional-guided treatment sessions may include additional therapeutic massage and/or manipulation sessions in which the professional manipulates the patient's body at or near the injury site in order to stimulate blood flow, minimize scar tissue formation, encourage muscle growth, and/or the like.

Historically, patients have been unable to recreate the therapeutic manipulation treatment offered by professionals between and/or after professional treatment sessions. Accordingly, a need exists for devices enabling patients to self-perform therapeutic manipulation treatment to further aid in recovery from bodily injury.

BRIEF SUMMARY

Various embodiments are directed to a therapy tape (e.g., a medical therapy tape, physiotherapy tape, physical therapy tape, chiropractic therapy tape, naprapathic therapy tape, massage therapy tape, lymphatic therapy tape, sports therapy tape, and/or the like) having one or more handles and/or one or more stimulators configured to enable a patient to continue manipulation and/or massage based treatment without the supervision of a medical professional. For example, the patient may be able to lift and/or move portions of the patient's skin to encourage rehabilitation and/or healing of portions of the patient's body onto which the tape has been secured. For example, the therapy tape may be configured to aid in treatment of strained, damaged, and/or weakened muscles and/or ligaments, hematoma, bruising, cording, spinal injuries, numbness, tissue and/or muscle tension and/or stiffness (e.g., from spasticity). The therapy tape may additionally be configured to aid in treatment of various bodily conditions, such as epicondylitis, plantar fasciitis, MS, fibromyalgia, swelling lymphedema, lipedema, and/or the like. In various embodiments, the therapy tape may be configured to aid in recovery from medical procedures (e.g., surgical procedures), such as dental procedures, plastic surgery, liposuction, and/or the like. The therapy tape may additionally be configured to provide treatment to prevent injury, to aid in comfort of the patient, and/or the like. For example, the therapy tape may be configured to trigger acupuncture points, pressure points, and/or the like. The therapy tape may additionally be configured to lift, stretch, and/or move tissue and/or anchor filaments connected with the tissue. The therapy tape may additionally be configured to provide support to various bodily portions (e.g., a limb), and/or the like. The therapy tape may be usable with adults, children, elderly patients, and/or the like. Moreover, in certain embodiments, the therapy tape may be usable with animals (e.g., horses, dogs, cats, and/or the like).

Accordingly, various embodiments are directed to a therapy tape comprising (i) a backing layer configured to conform to a portion of a patient's body, wherein the flexible backing layer defines a top side and a bottom side opposite the top side; (ii) an adhesive material secured relative to the bottom side of the flexible backing layer, wherein the adhesive material is configured to adhere the backing layer against a patient's skin; and (iii) one or more handles secured relative to the top side of the flexible backing layer, wherein the one or more handles are secured to the flexible backing layer via one or more fasteners. In certain embodiments, the adhesive material is configured to maintain adherence with the backing layer and the patient's skin while the handles are pulled normal to the patient's skin. In various embodiments, the adhesive material is secured to the backing layer such that the adhesive material and the backing layer do not substantially delaminate upon removal from the patient's skin.

In various embodiments, the backing layer is inelastic. Moreover, the adhesive material may be heat activated by the patient's body heat. Moreover, in certain embodiments, the one or more fasteners comprise a second adhesive material different from said adhesive material, wherein the second adhesive material is configured to permanently secure the one or more handles relative to the top side of the flexible backing layer. In certain embodiments, the one or more fasteners comprise thread sewn through at least a portion of each of the one or more handles and the backing layer. Moreover, at least one of the one or more handles may comprise a single-ply flexible sheet secured relative to the backing layer. Moreover, in certain embodiments, the one or more handles comprise a base portion configured to be secured onto the top side of the backing layer and a grip portion extending away from the base portion. In certain embodiments, the base portion of the one or more handles are secured relative to the top side of the backing layer via the one or more fasteners.

In various embodiments, the backing layer defines a length and a width measured perpendicular to the length, wherein the length is substantially longer than the width. In certain embodiments, at least one of the one or more handles extends across the backing layer in a direction parallel with the width of the backing layer. In alternative embodiments, at least one of the one or more handles extends across the backing layer in a direction parallel with the length of the backing layer. In certain embodiments, the one or more handles are detachably secured relative to the backing layer, and wherein the one or more fasteners are selected from: magnets, hook-and-loop fasteners, or snap-fasteners.

In various embodiments, the therapy tape additionally comprises one or more stimulators configured to apply a stimulating signal to a patient's skin. The one or more stimulators may comprise at least one of: a vibration element, a pressure applicator, or a TENS device. Moreover, the therapy tape may comprise a controller configured to generate one or more stimulator signals to selectively activate the one or more stimulators; wherein the controller comprises at least one communication interface configured to receive data transmitted from at least one external computing entity. In certain embodiments, the communication interface is a wireless communication interface.

Various embodiments are directed to a method for manipulating a flexible material (e.g., skin). The method may comprise steps for: (i) securing a tape structure against a surface of the flexible material, wherein the tape structure comprises: a backing layer configured to conform to a portion of the surface of the flexible material, wherein the flexible backing layer defines a top side and a bottom side opposite the top side; an adhesive material secured relative to the bottom side of the flexible backing layer, wherein the adhesive material is configured to adhere the backing layer against the surface of the flexible material; and one or more handles secured relative to the top side of the flexible backing layer, wherein the one or more handles are secured to the flexible backing layer via one or more fasteners; and (ii) applying a tensile force to at least one of the one or more handles to lift a portion of the backing layer and a secured portion of the surface of the flexible material.

In various embodiments, the one or more handles are detachably secured relative to the top side of the flexible backing layer, and accordingly the method may further comprise steps for securing one or more handles relative to the top side of the flexible backing layer via one or more detachable fasteners. Moreover, in various embodiments, the adhesive material is heat activated, and accordingly the steps for securing the tape structure against a surface of the flexible material may comprise: placing the adhesive material of the tape structure against the patient's skin; and raising the temperature of the adhesive material based on the patient's body heat to securely adhere the adhesive material to the patient's skin. Moreover, in certain embodiments, the backing material is inelastic, such that applying a tensile force to at least one of the one or more handles causes at least a portion of the surface of the flexible material to displace in a direction of the tensile force by a distance at least substantially equal to a displacement of a handle.

BRIEF DESCRIPTION OF THE SEVERAL VIEWS OF THE DRAWINGS

Reference will now be made to the accompanying drawings, which are not necessarily drawn to scale, and wherein.

DETAILED DESCRIPTION

The present invention will now be described more fully hereinafter with reference to the accompanying drawings, in which some, but not all embodiments of the invention are shown. Indeed, the invention may be embodied in many different forms and should not be construed as limited to the embodiments set forth herein. Rather, these embodiments are provided so that this disclosure will satisfy applicable legal requirements. Like numbers refer to like elements throughout.

In various embodiments, therapy tapes comprise handles (e.g., detachable and/or secured relative to a backing layer) and/or stimulators (e.g., vibrators, pressure applicators, transcutaneous electrical nerve stimulation devices (TENS devices), and/or the like) to facilitate therapeutic treatment of a patient injury, disability, medical treatment site, and/or the like. The therapy tape may comprise a backing material configured to support additional features of the tape, an adhesive layer configured to selectably secure the tape against a surface of a flexible material (e.g., a patient's skin), one or more handles, and/or one or more stimulators. The handles may be integrated into the tape to enable a healthcare professional (e.g., physician, physical therapist, and/or the like), the patient, and/or another individual to manipulate the material (e.g., skin). For example, the handles may enable the healthcare professional and/or the patient to pull, stretch, twist, extend, elongate, and/or the like the underlying skin, tissue, fascia, and/or the like as a part of a medical treatment (e.g., a medical treatment including stretching, pulling, pushing, twisting, and/or the like the underlying skin, tissue and/or fascia of a patient) to encourage blood flow within and/or proximate the skin to which the tape is secured, to break-up and/or discourage scar tissue development, to encourage muscle development, to improve lymphatic flow and/or drainage, to increase fluid flow within a patient's body, to increase metabolic rate of a patient's body, and/or the like. Accordingly, the adhesive layer of the tape may be configured to be securely fastened against the patient's skin such that pulling and/or manipulating one or more handles of the tape does not cause the tape to detach from the patient's skin. Moreover, the therapy tape may be configured to vary in length and/or width, for example, as it is stretched, compressed, and/or the like.

Moreover, in various embodiments, the therapy tape may comprise one or more stimulators configured to stimulate the patient's skin while the tape is secured to the patient. In various embodiments, the therapy tape may comprise an integrated controller comprising a power supply and/or one or more control devices configured to selectably activate and/or deactivate the one or more stimulators. In various embodiments, the controller may be configured for wireless and/or wired connection with an external computing device (e.g., handheld computing device, desktop computing device, laptop computing device, control panel, and/or the like). The controller may be configured to transmit signals to the computing device indicative of current and/or historical status of the one or more stimulators, and/or may be configured to receive one or more control signals from the external computing entity configured to manipulate operation of the one or more stimulators.

In various embodiments, therapy tape may comprise a plurality of stimulators (e.g., a plurality of stimulators of the same type and/or a variety of types of stimulators) and/or one or more handles. Accordingly, the therapy tape may be configured to provide a variety of therapy types for the patient.

In various embodiments, the therapy tape may be configured to remain secured against a patient for an extended period of time (e.g., greater than one day). In such embodiments, the therapy tape may be configured to enable a patient to self-provide therapy when not in direct communication with a healthcare professional.

Figure 8:
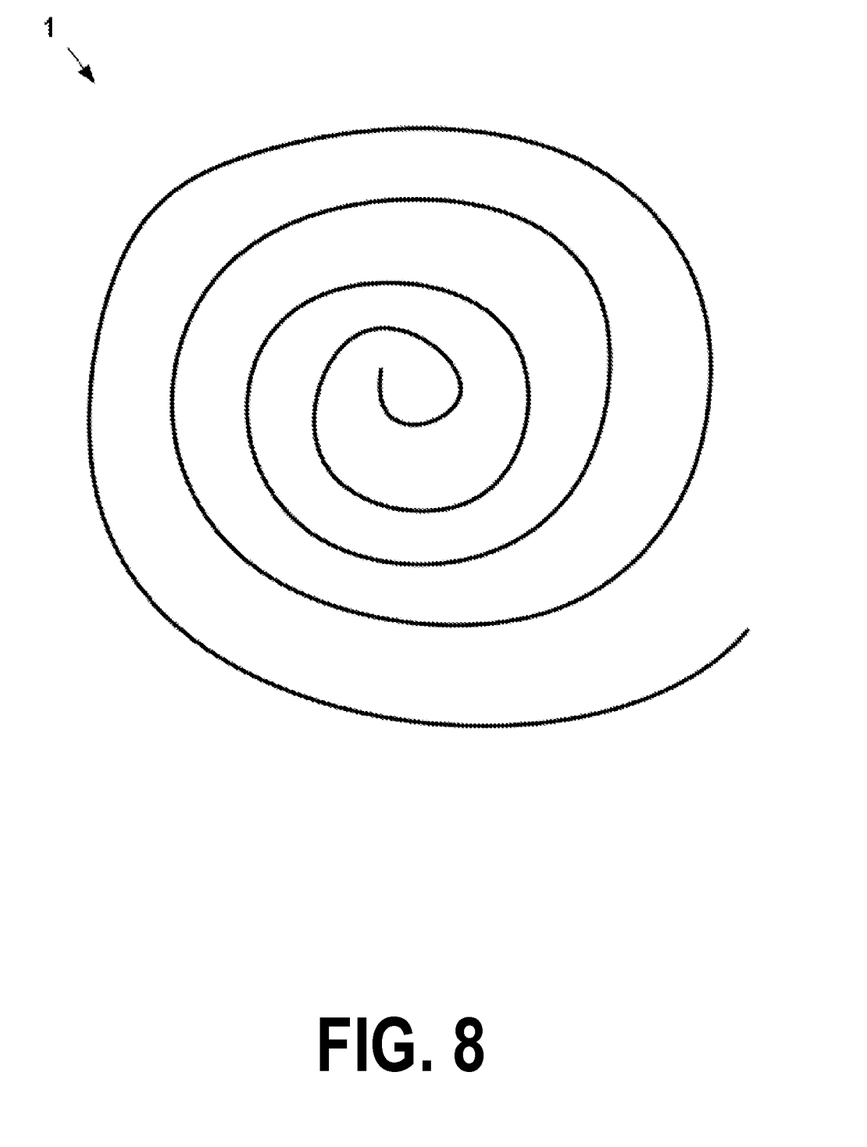
FIG. 8 shows a side view of an example therapy tape.

As discussed herein, the therapy tape may have a length and a width. In certain embodiments, the length of the therapy tape may be significantly longer than the width, such that the therapy tape may be rolled (e.g., onto a roll) for storage and/or distribution (shown in FIG. 8). As just one non-limiting example, the therapy tape may have a width of at least approximately 1-inch and a length of at least 6 inches (e.g., a length of 3-feet, 6-feet, 12-feet, 50-feet, 100-feet, and/or the like). As will be discussed in greater detail herein, the therapy tape may be configured to be stored on a roll, and a length of tape may be removed and detached (e.g., cut) from the roll for use. However, it should be understood that the therapy tape may have any proportion and/or relative dimensions. For example, in certain embodiments, the width may be larger than the length. Moreover, in certain embodiments, the therapy tape may vary in length (e.g., across the width of the tape) and/or width (e.g., across the length of the tape).

Backing Layer

In various embodiments, a therapy tape may comprise a backing layer having an adhesive layer secured thereto. In certain embodiments, the backing layer may additionally have one or more handles and/or one or more stimulators secured thereto.

The backing layer may comprise a woven or nonwoven material, such as a woven fabric, a nonwoven film, a nonwoven fabric, and/or the like. In various embodiments, the backing layer may comprise a single layer, however in certain embodiments, the backing layer may comprise a plurality of layers (e.g., a woven layer and a non-woven layer). In certain embodiments, the backing layer may comprise a plurality of fibers (e.g., woven fibers, blown fibers, and/or the like). The plurality of fibers may comprise reinforcing fibers having a high tensile strength and configured to impede undesirable tearing and/or breaking of the tape. Moreover, in certain embodiments, the plurality of fibers may comprise elastic fibers configured to enable the backing layer to reversibly stretch in one or more directions.

In various embodiments, the backing layer may comprise one or more natural and/or synthetic materials. For example, the backing layer may comprise plant-based materials (e.g., cotton, wood fibers, bamboo fibers, cellulose fibers, natural rubber, and/or other biodegradable materials) synthetic materials, (e.g., polyester, synthetic rubber, polyvinyl chloride, and/or the like), and/or the like. In various embodiments, the backing layer may be hydrophobic, such that the backing layer may dry quickly when exposed to a moist environment (e.g., sweat, water, and/or the like). However, in certain embodiments, at least a portion of the backing material may be hydrophilic. As specific examples, the backing layer may comprise a Kinesiology tape backing layer, a medical support tape backing layer, an athletic tape backing layer, a dynamic tape backing layer, and/or the like. In various embodiments, the backing layer may comprise a plurality of materials. For example, a first portion of a backing layer may comprise a first material and a second portion of the backing layer may comprise a second material. As a specific example, a first portion of the backing layer may comprise a flexible, inelastic material and a second portion of the backing layer may comprise a flexible, elastic material.

In various embodiments, the backing layer may be a porous material, having a plurality of pores extending therethrough between a top surface and a bottom surface. For example, the pores may extend between fibers of a woven material, and/or through openings within a nonwoven material. Accordingly, the backing layer may be breathable, thereby allowing gases (e.g., air) to flow through the backing layer. Accordingly, the backing layer may enable air to flow to and/or away from a patient's skin located adjacent the therapy tape when secured thereto.

In various embodiments, the backing layer may be stretchable and/or elastic in one or more directions. For example, the backing layer may be stretchable and/or elastic in a direction parallel to the length of the tape and/or in a direction parallel to the width of the tape. Accordingly, in certain embodiments, the backing may be configured to provide a tensile force to a patient's skin when the therapy tape is secured thereto. For example, the elastic backing layer (and accordingly the remainder of the therapy tape) may be stretched during application to a patient and released once applied. Accordingly, the therapy tape may thus apply a tensile force as a result of the stretched elastic backing layer attempting to return to its original, unstretched form. However, it should be understood that in certain embodiments, the backing layer may be inelastic and may resist stretching (e.g., elongating). As will be discussed in greater detail herein, embodiments utilizing an inelastic backing layer may provide direct feedback to a patient's skin when manipulating the therapy tape (e.g., via handles). For example, because the backing layer does not stretch, displacing a portion of the therapy tape (e.g., via a handle) causes an at least substantially equal displacement of skin to which the therapy tape is secured.

Adhesive Layer

As discussed herein, the therapy tape may comprise an adhesive layer secured to the backing layer. The adhesive layer may be configured to selectably secure the therapy tape against a patient's skin. Accordingly, the adhesive layer may be secured against the backing layer such that the adhesive layer and backing layer do not delaminate during application and/or removal from the patient.

In various embodiments, the adhesive layer may be secured against the backing layer via any of a variety of processes, as discussed in greater detail herein. For example, the adhesive layer may comprise an adhesive sheet laminated against the backing layer, an adhesive spray sprayed onto the backing layer, an adhesive liquid rolled onto the backing layer, dripped onto the backing layer, and/or the like.

In various embodiments, the adhesive layer may be continuous, such that at least substantially an entire surface of the backing layer is covered with the adhesive layer. However, in certain embodiments, the adhesive layer may be discontinuous, and may thus comprise a plurality of spaced adhesive portions secured to a surface of the backing layer. For example, the adhesive layer may comprise a plurality of spaced rectangular, circular, triangular, and/or the like adhesive portions therein. In various embodiments, the adhesive layer may be breathable (e.g., through adhesive portions and/or between adhesive portions) such that gases (e.g., air) may flow through the backing layer and the adhesive layer.

Like the backing layer, the adhesive layer may be elastic and/or stretchable, such that the elastic layer may move and/or stretch with the backing layer. Accordingly, the adhesive layer may be configured to conform with the movement of the backing layer such that the adhesive layer does not provide any force relative to the backing layer that may cause the adhesive layer to delaminate from the backing layer.

In various embodiments, the adhesive layer may be configured to detachably secure the therapy tape against a patient's skin. In various embodiments, the adhesive layer may provide sufficient tensile strength between the therapy tape and the patient's skin that manipulating the therapy tape (e.g., via handles) may cause relative manipulation of the patient's skin, and the therapy tape may remain secured to the patient's skin. In various embodiments, the adhesive layer may have a low shear strength to facilitate removal of the therapy tape from the patient, such as by stretching the therapy tape relative to the patient's skin. In various embodiments, the adhesive may comprise an acrylic polymer. As just one non-limiting example, the adhesive layer may comprise Stratagel® adhesive material offered by Nitto Denko.

In certain embodiments, the adhesive layer may be heat-activated to enable the therapy tape to be secured to a patient's skin and/or to be removed from the patient's skin. Accordingly, the therapy tape may be secured to a patient's skin, and the patient's body heat may sufficiently heat the therapy tape to activate the adhesive layer such that the tape is secured relative to the patient's skin. Once activated and secured to the patient's skin, the therapy tape may be manipulated together with the patient's skin (e.g., via handles) without the therapy tape become dislodged from the patient's skin.

Handle

With reference to the figures, the therapy tape may comprise one or more handles secured relative to the backing layer to enable lifting of the therapy tape and the underlying flexible material (e.g., skin) to which it is secured. The therapy tape may have a single handle and/or a plurality of handles having any of a variety of configurations. In various embodiments as discussed herein, the handles may be hook-shaped, circular, "U"-shaped, "D"-shaped, and/or the like. For example, in various embodiments handles may be O-rings, U-rings, J-rings, D-rings, and/or the like. Moreover, in various embodiments, the handles of the therapy tape may be secured relative to the backing layer such that the handle concentrates tensile forces applied to the handle along a center portion of the backing layer in order to impede peeling of the tape from the applied patient's skin.

Figure 1A:
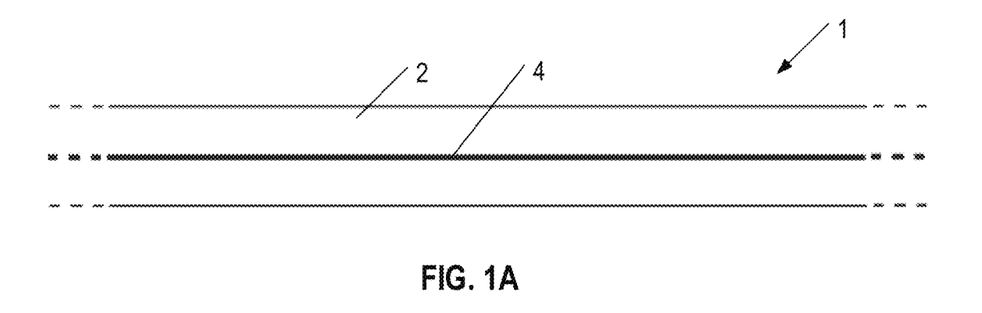
FIGS. 1A-1C show top and side views of various therapy tape embodiments.
Figure 1B:
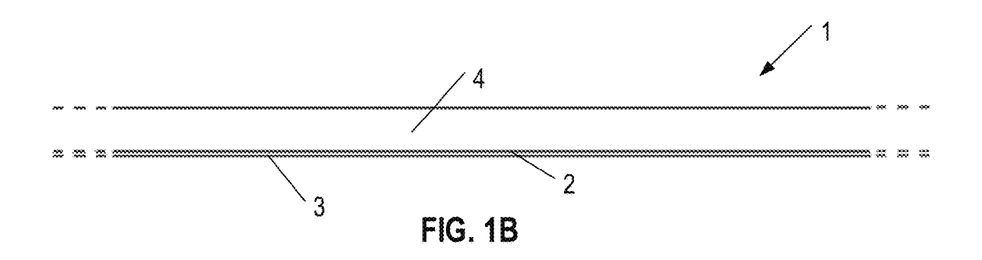
Figure 1C:
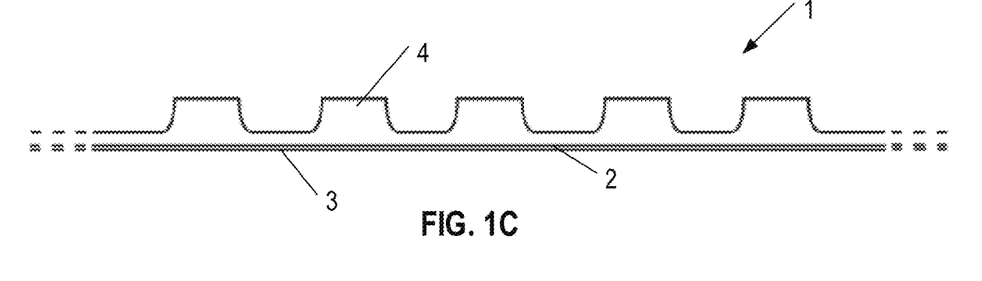

As shown in FIGS. 1A-1C, the therapy tape 1 comprises one or more handles 4 oriented at least substantially parallel with the length of the tape 1. As shown in FIG. 1A, which shows a top view of the tape 1, the therapy tape 1 may comprise a backing layer 2 and a handle 4 positioned at least substantially centrally with the therapy tape 1. As will be discussed herein, the handle 4 may be continuous with the backing layer 2, and may be defined by a folded portion of the backing layer 2. However, in various embodiments, the handle 4 may be a separate component from the backing layer 2 that is secured relative to the backing layer 2 with one or more fasteners (e.g., sewn threads, adhesive, knitting, magnets, zippers, ties, laces, rivets, and/or the like). In various embodiments, the handle 4 may comprise a flexible, inelastic, and/or elastic material (e.g., fabric, plastic, and/or the like) to enable the handle 4 to pivot and/or otherwise flex relative to the backing layer 2. In certain embodiments, the handle 4 may comprise the same material as the backing layer 2, although in certain embodiments, the handle 4 may comprise a material different from the backing layer 2. However, it should be understood that in certain embodiments, the handle may comprise a rigid material (e.g., wood, metal, plastic, and/or the like). For example, the handle 4 may comprise a Kinesiology tape material, a medical support tape material, an athletic tape material, a dynamic tape material, and/or the like. As yet other examples, the handle 4 may comprise any of the materials provided as example backing layer materials discussed herein. Moreover, in certain embodiments, the handle may comprise multiple materials. For example, a first portion of a handle may comprise a first material and a second portion of a material may comprise a second material. For example, a first portion of a handle may comprise a flexible, inelastic material, and a second portion of the handle may comprise a flexible, elastic material.

As shown in FIG. 1B, which illustrates a side view of the therapy tape 1, the handle 4 may extend away from the backing layer 2 (e.g., at least substantially perpendicular from the backing layer 2). The handle 4 may be secured to a top side of the backing layer 2, opposite a bottom side of the backing layer 2 to which the adhesive layer 3 is secured. As discussed herein, the adhesive layer may be configured to detachably secure the therapy tape 1 relative to a patient's skin.

As shown in FIGS. 1B and 1C, the handle 4 may be continuous along the length of the tape 1 and/or discontinuous along the length of the tape 1. As discussed herein, the handle 4 may be secured relative to the backing layer 2 such that tensile forces applied to the handle are concentrated along a central portion to impede delamination of the therapy tape 1 from the patient's skin while a tensile force is applied to the patient's skin. For example, then handles 4 may comprise one or more materials configured to concentrate a tensile force along a central portion of the therapy tape 1. In various embodiments, the handle 4 may be configured to distribute a tensile force along at least a portion of the tape in a linear distribution, a parabolic distribution, and/or the like. For example, the tensile force may be concentrated in a central portion of the tape and the amount of tensile force applied to the tape may decrease (e.g., linearly, exponentially, hyperbolically, and/or the like) approaching the edge of the tape. The handle 4 may comprise one or more elongated portions extending away from the backing layer 2 and/or one or more short portions extending away from the backing layer 2. The elongated portions and/or the short portions may have any of a variety of shapes, such as rectangular, elliptical, half-circular, triangular, and/or the like. In various embodiments, the relative shape and/or positioning of the handle portions may be determined during and/or after application to a patient's skin. For example, a handle elongated portion may be defined (e.g., via cutting and/or securing to the backing layer 2) proximate a point of interest in the patient's skin (e.g., a proximate point of injury).

Figure 2A:
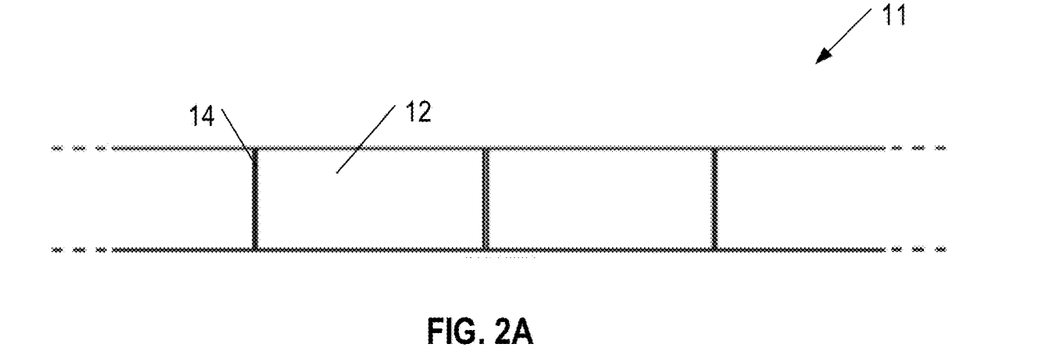
FIGS. 2A-2D show top and side views of various therapy tape embodiments.
Figure 2B:
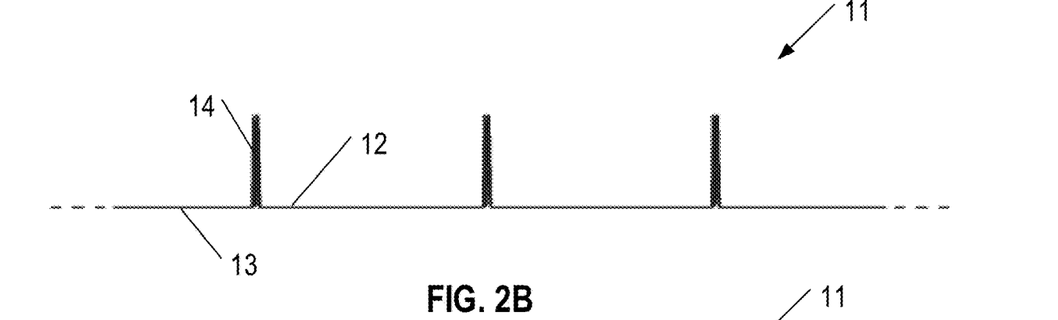

With reference now to FIGS. 2A-2D, a therapy tape 11 may comprise a plurality of handles 14 oriented at least substantially perpendicular to the length of the therapy tape 11. In various embodiments, the handles 14 may extend between at least approximately 0.001 inches-48 inches away from the backing layer. As just one example, the handles may extend between about 0.5 inches-6 inches away from the backing layer. As a specific example, the handles may extend between about 1 inch-2 inches away from the backing layer. Therapy tape 11 may have a similar configuration to therapy tape 1 (e.g., materials, handle securing fasteners, and/or the like), however therapy tape 11 may have a different handle orientation relative to the length of the therapy tape 11. As shown in FIGS. 2A-2D, therapy tape 11 may comprise handles 14 extending away from a top surface of backing layer 12 (opposite adhesive layer 13), and at least substantially perpendicular to the length of therapy tape 11. As shown in FIG. 2B, the handles 14 may be formed from looped portions of the backing layer 12 extending upwardly away from a primary plane of the backing layer 12 (e.g., plane against which the patient's skin is positioned). The looped portion of the backing layer 12 may be fastened together (e.g., by sewn thread, by adhesive, and/or the like) to form handles 14. In embodiments in which adhesive is utilized to secure form the handles 14 utilizing lengths of looped backing layer 12, the adhesive utilized to securely form the handles 14 may be different from the adhesive utilized to secure the therapy tape against a patient's skin.

Figure 2C:
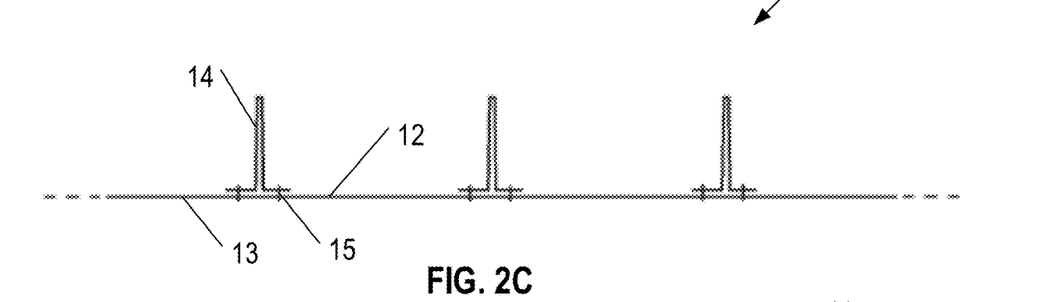
Figure 2D:
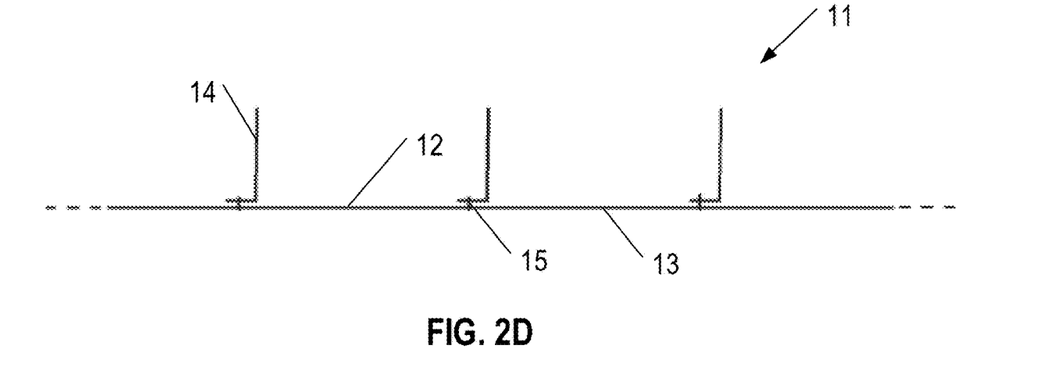

FIGS. 2C-2D illustrate alternative embodiments for securing handles 14 relative to backing layer 12. As shown in FIG. 2C, the handle 14 may comprise a base portion configured to be secured adjacent and/or parallel with a backing layer, and a grip portion extending away from the base. The base portion may comprise one or more material layers (e.g., a single layer) and the grip portion may comprise at least the same number of material layers as the base portion (e.g., a single layer or two layers). In various embodiments, the handles 14 may comprise a folded material secured relative to the backing layer 12. In such embodiments, the folded layers of the handle 14 may form the base portion and the grip portion such that the base portion may be secured relative to the backing layer, and the folded portion forming the grip portion may be secured together. For example, one or more folded layers forming the grip portion may be secured relative to one another using a fastener 15 as discussed herein (e.g., sewn thread, adhesive, and/or the like). As shown in FIG. 2C, the base portion of the folded layers may be secured relative to the backing layer 12 using one or more fasteners 15 (e.g., sewn thread, adhesive, and/or the like). In various embodiments, the base portion may define an enlarged area to be secured against the backing layer. Accordingly, when a tensile force is applied to the handle (e.g., grip portion) as discussed herein, the enlarged base portion may serve to distribute the effect of the tensile force across an area of the backing layer, thereby distributing the tensile force across a larger area of the patient's skin to discourage the backing layer from becoming dislodged from the patient's skin during treatment. For example, in embodiments in which the handles 14 are at least substantially aligned perpendicular to the length of the backing layer 12, the base portion may have a width at least substantially equal to the backing layer 12, and a length of at least 1 inch. In various embodiments, the base portion may have a length between 1 inch and 12 inches.

In embodiments in which the handles 14 are oriented at different angles relative to the backing layer 12, the base portion of the handles may be positioned entirely adjacent the backing layer 12, such that no portion of the base portion extends beyond the edges of the backing layer 12. In certain embodiments, the base layer may have a substantially equal size and shape as the backing layer 12.

FIG. 2D shows yet another example embodiment for securing handles 14 relative to backing layer 12. As shown in FIG. 2D, each handle may comprise a single layer of material (e.g., fabric, plastic, and/or the like) secured relative to the backing layer 14 with one or more fasteners 15 (e.g., sewn thread, adhesive, and/or the like).

In various embodiments, handles 14 may be formed and/or secured relative to backing layer 12 during and/or after securing the therapy tape 11 relative to a patient's skin. Accordingly, the handles 14 may be positioned by a user (e.g., a healthcare professional) based on therapeutic needs of the patient. For example, the handles 14 may be secured relative to the therapy tape 11, and therefore relative to the patient, based on the location of an injury, and/or the like.

Figure 3:
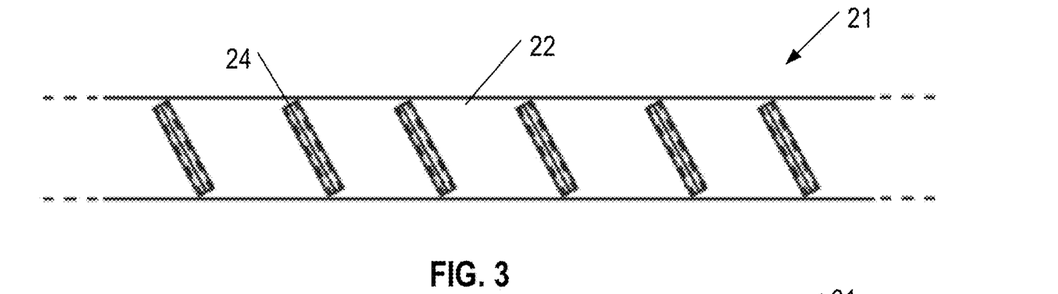
FIG. 3 shows a top view of an example therapy tape embodiment.

As shown in FIG. 3, which shows a therapy tape 21 having a configuration similar to therapy tapes 1 and 11 discussed here. Therapy tape 21 may comprise a backing layer 22 to which one or more handles 24 are secured. As shown in FIG. 3, handles 24 may be secured at any orientation relative to the backing layer 22. The handles 24 may be secured using any of a variety of configurations as discussed herein (e.g., formed as folded portions of backing layer 22, formed as folded portions of material secured relative to backing layer 22, formed as single layers of material secured relative to backing layer 22, and/or the like).

With reference to FIGS. 4A-4D, therapy tape 31 may be configured such that handles may be detachably secured relative to backing layer 32. In the illustrated embodiments of FIGS. 4A-4D, backing layer 32 and adhesive layer 33 may have a configuration similar to those described in reference to therapy tapes 1, 11, and 21 above. However, as shown in FIGS. 4A-4D, therapy tape 31 may additionally comprise one or more connecting portions 36 secured relative to backing layer 32 that is configured to enable one or more handles 37 to be detachably secured relative to the therapy tape 31. In various embodiments, connecting portions 36 may comprise any of a variety of detachable fastener materials, such as hook-and-loop material (e.g., Velcro®), magnetic material, detachable and/or permanent adhesive, snaps, and/or the like. As just one example, the adhesive material of the adhesive layer 33 may be continued onto the backing layer 32, such that handles 37 may be secured relative to the adhesive material on the backing layer.

Figure 4A:
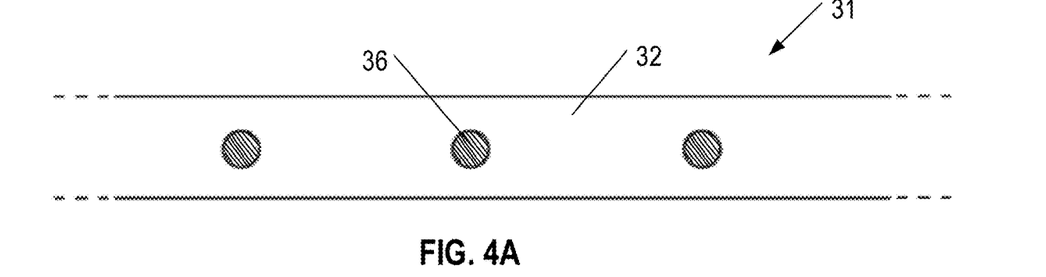
FIGS. 4A-4D show top and side views of various therapy tape embodiments.
Figure 4B:
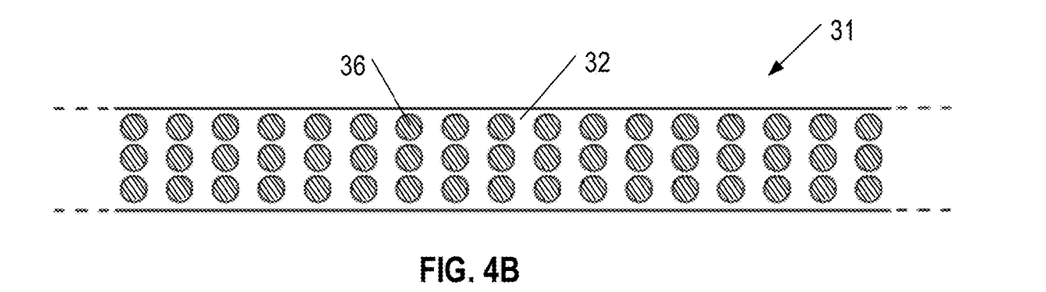
Figure 4C:
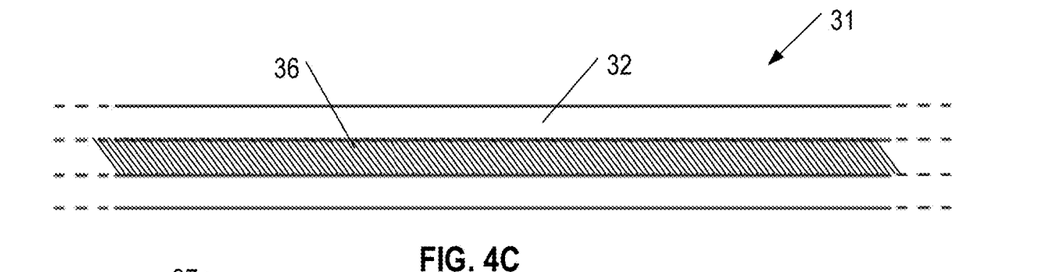

As shown in FIGS. 4A-4D, the connecting portions 36 may comprise continuous connecting portions 36 (e.g., as shown in FIG. 4C) and/or discontinuous connecting portions 36 (e.g., as shown in FIGS. 4A-4B). In various embodiments, each connecting portion 36 may be configured to be secured relative to a detachable handle 37. For example, each connecting portion 36 may comprise a female snap connector configured to be secured relative to a male snap connector of a detachable handle 37. In yet other embodiments, a plurality of connecting portions 36 may be configured to be secured relative to a single detachable handle 37. For example, in the illustrated embodiment of FIG. 4B, a plurality of connecting portions 36 may be configured to engage a detachable handle 37 simultaneously to secure the detachable handle 37 relative to the therapy tape 31.

Figure 4D:
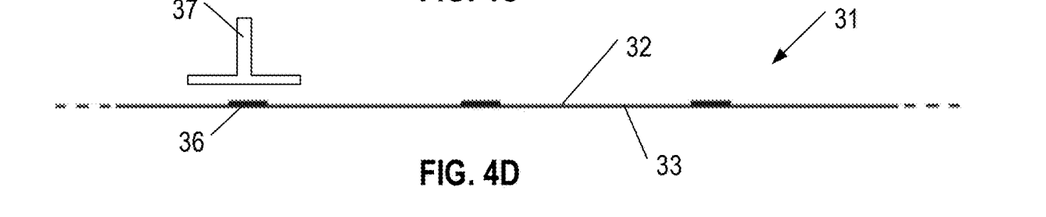

As shown in FIG. 4D, the connecting portions 36 may have a low profile to avoid unintentionally snagging items placed adjacent the therapy tape 31 (e.g., clothes). Moreover, in various embodiments, the one or more connecting portions 36 may be configured to enable a detachable handle 37 to be secured relative to the therapy tape 31 through one or more additional layers (e.g., clothing layers). Thus, for example, the therapy tape 31 may be secured to a patient's skin under the patient's clothes, and a detachable handle 37 may be configured to engage to connecting portion 36 through the patient's clothes (e.g., via magnetic force) to enable the patient and/or healthcare professional to manipulate the therapy tape 31 and the secured patient's skin through the patient's clothes.

In various embodiments, connecting portions 36 may be secured relative to a top side of backing layer 32 (e.g., opposite adhesive layer 33). In such embodiments, connecting portions 36 may be secured to the backing layer 31 via one or more fasteners (e.g., sewn thread, adhesive, rivet, and/or the like). In certain embodiments, connecting portions 36 may be secured adjacent bottom side of the backing layer 32 (e.g., between backing layer 32 and adhesive layer 33 or on an opposite side of the adhesive layer 33 relative to backing layer 32). In such embodiments, the connecting portions 36 may be secured relative to the backing layer 32 via the adhesive properties of adhesive layer 33, and/or via an additional fastener (e.g., an additional adhesive, sewn thread, and/or the like).

Like handles 4 and 14, connecting portions 36 may be secured relative to the backing layer 32 during and/or after securing the therapy tape 31 relative to the patient. For example, the connecting portions 36 (e.g., magnets) may be placed between the adhesive layer 33 and the patient's skin, such that the connecting portions 36 are pinned between the therapy tape 31 and the patient's skin. As yet another embodiment, the connecting portions 36 may be secured relative to a top side of the backing layer 32 during and/or after securing the therapy tape 31 relative to the patient's skin.

In various embodiments, the detachable handle 37 may comprise a rigid component and/or a flexible component. For example, the detachable handle 37 may comprise a magnetic material configured to be magnetically secured relative to a magnetic connecting portion 36. As yet another example, the detachable handle 37 may comprise a grip portion (e.g., a flexible grip portion and/or a rigid grip portion) configured to enable a user (e.g., patient and/or healthcare professional) to manipulate the detachable handle 37 and a connector configured to engage the connecting portion 36 of the therapy tape 31. For example, the connector may comprise a mating hook-and-loop material configured to be secured relative to a corresponding hook-and-loop connecting portion 36. As yet another example, the connector of the detachable handle 37 may comprise a snap-type connector (e.g., a male snap-type connector) configured to engage a corresponding snap-type connector (e.g., a female snap-type connector) of a connecting portion 36.

In various embodiments, the therapy tape may comprise one or more handles (e.g., handles 4, 14, 24) and one or more connecting portions 36 configured to detachably secure one or more detachable handles 37 relative to the therapy tape.

Stimulators and Controller

Figure 5:
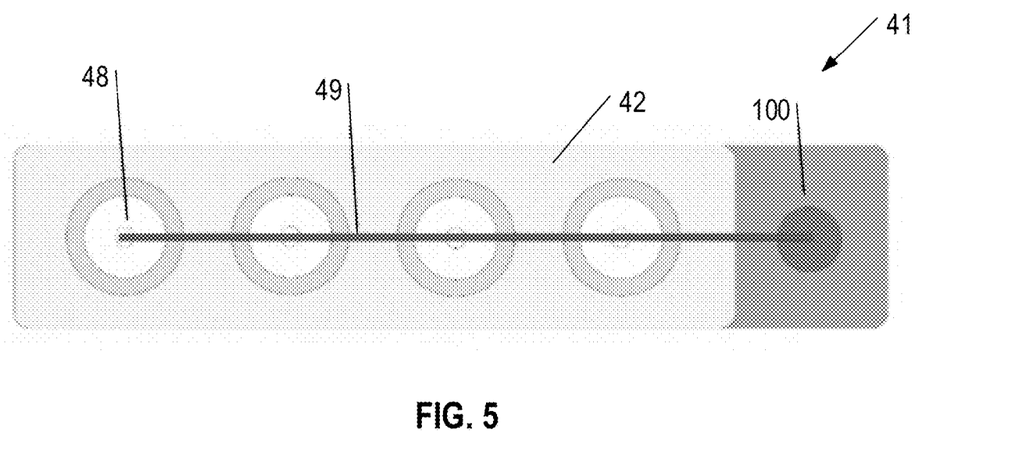
FIG. 5 shows a top view of a therapy tape comprising various stimulators according to one embodiment.
Figure 6A:
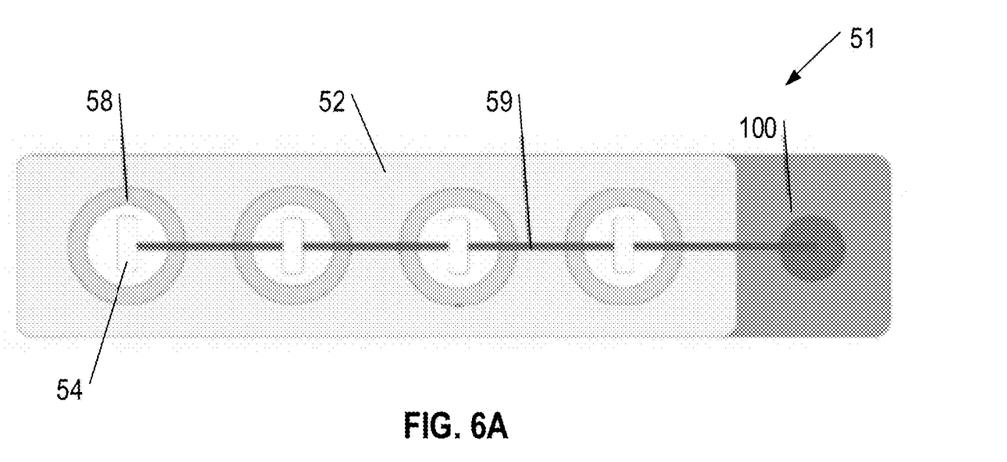
FIGS. 6A-6B show top and side views of a therapy tape comprising stimulators according to one embodiment.
Figure 6B:
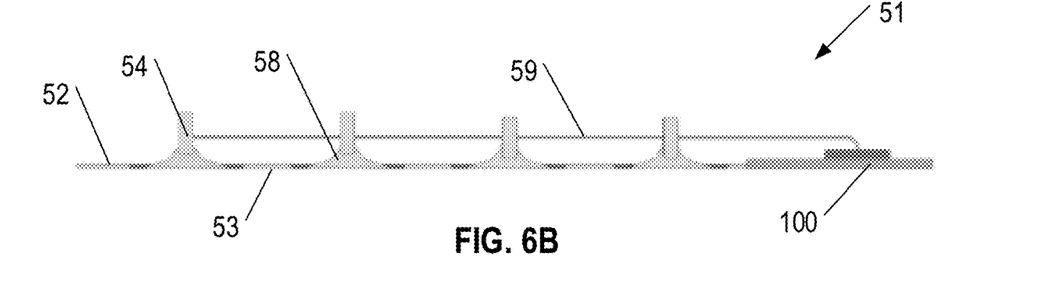
Figure 6C:
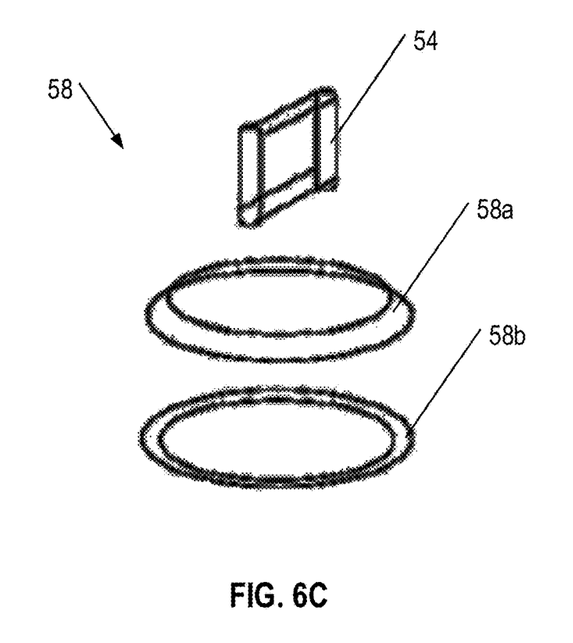
FIG. 6C shows an exploded view of a stimulator and handle according to one embodiment.
Figure 7:
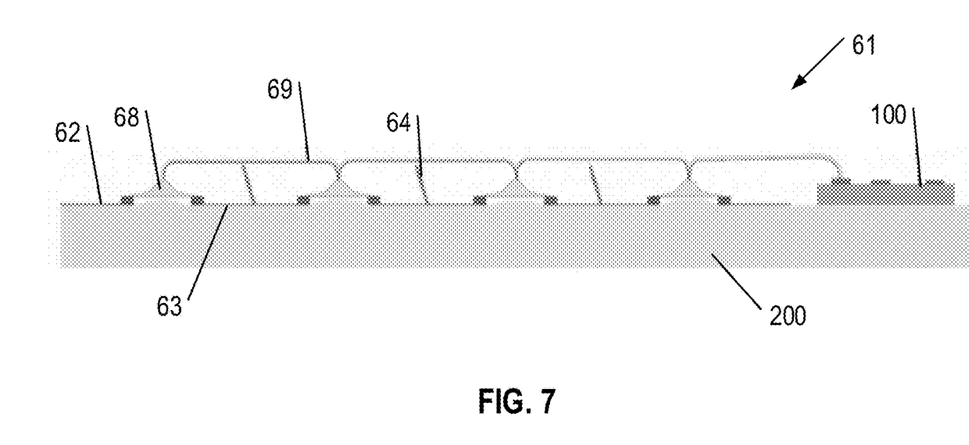
FIG. 7 shows a side view of an example therapy tape comprising stimulators secured against a patient's skin according to one embodiment.

With reference to FIGS. 5-7, the therapy tape may comprise one or more stimulators (e.g., vibration element, pressure applicators, TENS devices, biofeedback devices, bio-impedance analysis devices, thermometers, pulse measurement devices, and/or the like) configured to provide stimulation to the skin to which the therapy tape is secured. As discussed herein, various embodiments of therapy tape may comprise a single vibration element, a plurality of vibration elements, a single pressure applicator, a plurality of pressure applicators, a single TENS electrode, a plurality of TENS electrodes, and/or the like. In various embodiments, a therapy tape may comprise one or more vibration elements and one or more pressure applicators. In yet other embodiments, a therapy tape may comprise one or more vibration elements and one or more TENS electrodes. In yet other embodiments, a therapy tape may comprise one or more pressure applicators and one or more TENS electrodes. In yet other embodiments, a therapy tape may comprise one or more vibration elements, one or more pressure applicators, and one or more TENS electrodes.

As shown in FIG. 5, the therapy tape 41 may comprise a backing layer similar to that discussed herein, with one or more vibration elements 48 secured thereto. In various embodiments, the one or more vibration elements 48 may be secured relative to a top side of the backing layer 42, a bottom side of a backing layer 42 (e.g., between backing layer 42 and adhesive layer (not shown) or opposite adhesive layer relative to the backing layer 42). As yet another embodiment, the therapy tape 41 may define one or more apertures extending therethrough (e.g., through backing layer 42 and/or adhesive layer) in which the vibration elements 48 are secured.

The one or more vibration elements 48 may comprise one or more vibration actuators configured to emit vibration pulses to a patient's skin to provide therapeutic sensations for the patient (e.g., pain relief, numbing, increased metabolic rate, and/or the like). In various embodiments, the one or more vibration elements 48 may be in electrical communication with a controller 100 (e.g., via electrical conduit 49) configured to emit power signals to each of the one or more vibration elements 48. In various embodiments, electrical conduit 49 may comprise one or more wires (e.g., solid and/or stranded), one or more printed electrical connectors (e.g., printed onto backing layer 42), and/or the like.

In various embodiments, the controller 100 may comprise a power supply (e.g., a battery) and a control circuit configured to emit signals to the one or more vibration elements 48. In various embodiments, the controller 100 may additionally comprise a communication interface configured to communicate with one or more external computing entities (e.g., a handheld computing device, such as a Personal Digital Assistant, a smartphone, a tablet, a smartwatch, and/or the like; a personal computing entity, such as a laptop computing device, a desktop computing device, and/or the like; and/or a central computing device, such as a server, a web interface, and/or the like). In various embodiments, the communication interface may be configured to communicate with one or more external communication interfaces via a wired interface and/or a wireless interface (e.g., Bluetooth®, Wi-Fi, Near Field Communication, LTE, 3G, and/or the like). In various embodiments, the communication interface may be configured to communicate via one or more networks, such as the Internet, an Intranet, and/or the like.

In various embodiments, the controller 100 may be configured to receive control signals from the external computing entity to control the one or more vibration elements 48. For example, the external computing entity may be configured to transmit signals indicative of a desired active/inactive state for the one or more vibration elements 48, a desired vibration frequency for the one or more vibration elements 48, and/or the like. For example, the external computing entity may be configured to generate and transmit the one or more control signals in response to receipt of user input indicative of desired operating characteristics of the vibration elements 48.

Although not shown, therapy tape 41 may additionally comprise one or more handles (e.g., similar to handles 4, 14, 24) and/or connecting portions 36 configured to be detachably secured to one or more detachable handles 37.

With reference now to FIG. 6A-6C, a therapy tape 51 may comprise one or more pressure applicators 58 (e.g., powered suction cups, compression sleeves, and/or the like) configured to provide pressure (e.g., negative pressure and/or positive pressure) to skin to which the therapy tape is secured 51. Each of the pressure applicators 58 may be in electrical and/or pneumatic communication with a controller 100 which may comprise a pump, an electrical actuator, and/or the like configured to provide pressure to each of the pressure applicators 58. For example, a conduit 59 extending from controller 100 to one or more of the pressure actuators 58 may comprise an electrical conduit (e.g., a wire) configured to transmit signals to each of the one or more pressure applicators 58 to cause each of the pressure applicators 58 to activate and provide pressure to the patient's skin. For example, each of the pressure applicators 58 may comprise actuators configured to apply a pressure to the patient's skin. In certain embodiments, the conduit 59 may comprise a pneumatic conduit (e.g., a tube) connecting a pump located at the controller 100 to each of the one or more pressure applicators 58. In such embodiments, the pump may be configured to pump air from the pressure applicators 58, thereby causing the pressure applicators to provide a pressure to the patient's skin.

FIG. 6B provides a side-view of a therapy tape 51 according to various embodiments. As shown in FIG. 6B, the pressure applicators 58 may additionally comprise one or more handles 54 extending therefrom. Each of the one or more handles 54 may have a configuration similar to handles 4, 14, and 24 as discussed herein. However, the handles 54 may be secured directly to the pressure applicators 58. As shown in FIG. 6C, handles 54 may extend from a top portion 58a of the pressure applicators 58, opposite a bottom portion 58b configured to contact a patient's skin. Although not discussed in reference to the vibration applicators 48 discussed above, it should be understood that vibration applicators 48 may additionally comprise handles 54 as discussed herein.

With reference to FIG. 7, various therapy tape 61 embodiments may comprise a plurality of stimulators 68. As shown therein, therapy tape 61 may comprise a plurality of stimulators 68 comprising vibrating elements configured to apply vibration stimulation to the patient's skin, pressure applicators configured to apply pressure to the patient's skin, and/or transcutaneous electrical nerve stimulation devices (TENS devices) configured to apply electrical stimulation to a patient's skin. Each of the stimulators 68 may be in electrical and/or pneumatic communication with a controller 100 via a conduit 69. As discussed herein, controller 100 may comprise one or more power sources, one or more electrical signal generators, and/or one or more pumps configured to actuate the one or more stimulators 68. Moreover, as shown in FIG. 7, the therapy tape 61 may comprise one or more handles 64 similar to handles 4, 14, and 24. Although not shown, therapy tape 61 may be configured to accept one or more detachable handles as discussed herein. In such embodiments, the therapy tape 61 may comprise one or more connecting portions 36 configured to engage one or more detachable handles 37.

Method of Manufacturing

In various embodiments, a therapy tape as discussed herein may be manufactured by forming and/or securing handles within and/or onto a backing material, and by applying an adhesive material to the backing material. Moreover, in various embodiments, a therapy tape may be formed as a portion of a large web (e.g., having a width equal to at least twice the width of the therapy tape) and the large web may be cut into individual therapy tape width portions. In certain embodiments, the therapy tape may be formed from a web of material at least substantially the same width as the therapy tape.

In various embodiments, the handles may be formed as a portion of the backing material by folding the backing material to form one or more loops therein. As discussed herein, the handles may align with the length of the therapy tape, and in such embodiments, the therapy tape may be contoured to form a loop extending above a top side of the backing material between lateral edges of the therapy tape. The looped portion of backing material may be fastened together (e.g., via an adhesive, sewn thread, rivets, and/or the like) to form one or more handles. In embodiments in which the handles extend laterally across the therapy tape between lateral edges of the therapy tape, a plurality of loops may be formed in the backing layer, for example, at various intervals (e.g., regular intervals and/or irregular intervals), and may be secured together with one or more fasteners.

A bottom side of the backing material, opposite the looped portion, may be coated with an adhesive material. In various embodiments, the adhesive material may be laminated onto the backing material, sprayed onto the backing material, screen printed onto the backing material, dripped onto the backing material, and/or the like. In certain embodiments, the adhesive material may be cured after being applied to the backing material, to form a strong mechanical bond between the backing layer and the adhesive material such that the adhesive material does not delaminate from the backing layer. After application of the adhesive material and formation of the handles, the therapy tape may be rolled onto a take-up roller for storage, shipping, and/or sale.

In various embodiments, the handles may be formed from a separate material and secured to the backing layer. For example, individual loops of material, strips of material, and/or the like may be secured to the backing layer via one or more fasteners (e.g., adhesive, sewn thread, rivets, and/or the like). For example, handles may be secured across the width of the therapy tape (e.g., extending between lateral edges). As yet another example, a handle may extend along the length of the therapy tape, and accordingly the handle may be secured along the length of the therapy tape.

In various embodiments, the adhesive material may be applied to the backing layer prior to forming the handles therein.

In embodiments comprising one or more connecting portions 36, the connecting portions may be secured to the backing layer via one or more fasteners (e.g., glue, sewn thread, rivets, and/or the like). In various embodiments, the connecting portions may be secured to a top side of the backing layer. However, it should be understood that in various embodiments, the connecting portions may be secured to the bottom side of the backing layer, while enabling a detachable handle to be secured relative to a top side of the backing layer. For example, one or more magnets may be secured to a bottom side of the backing layer (e.g., below adhesive layer or between adhesive layer and backing layer) to enable a detachable handle to be secured relative to a top side of the backing layer. In yet other embodiments, the backing layer may comprise a plurality of layers (e.g., two layers) secured together (e.g., with one or more fasteners) in such embodiments, the one or more connecting portions may be secured between two or more of the layers of the backing material.

Moreover, in embodiments in which the therapy tape comprises one or more stimulators, the stimulators may be secured relative to a bottom side of the therapy tape (e.g., below adhesive layer and/or between adhesive layer and backing layer). In yet other embodiments, the stimulators may be secured relative to a top side of the therapy tape. In yet other embodiments, one or more apertures may be formed within the therapy tape extending through the top side and bottom side of the therapy tape, and the one or more stimulators may be secured within the formed apertures. Moreover, a conduit (e.g., electrical conduit and/or pneumatic conduit, may be secured relative to each of the one or more stimulators. Moreover, a controller may be secured relative to the backing material (e.g., relative to a top side of the backing material, relative to a bottom side of the backing material, or relative to an end of the backing material), and the conduit may be secured relative to the controller. In various embodiments, the therapy tape comprising the one or more stimulators may be cut to a predefined length (e.g., 6 inches, 12 inches, 36 inches, and/or the like) and a controller may be secured relative to each length of therapy tape. In various embodiments, a protective sheet (e.g., a paper sheet, a wax paper sheet, a foil, and/or the like) may be secured relative to the adhesive layer to impede the adhesive layer from unintentionally becoming adhered to one or more surfaces.

Method of Use

As discussed herein, various embodiments of the described therapy tape may be utilized to provide therapeutic treatment of one or more ailments of a patient. For example, the described therapy tape may be configured to increase blood and/or other fluid flow to various portions of a patient's body, to relieve muscle pressure in various portions of a patient's body, to discourage formation of scar tissue, and/or the like.

In use, therapy tape having one or more handles secured thereto may be adhered to a patient's skin. In various embodiments, a length of therapy tape may be removed from a roll of therapy tape (e.g., by cutting a selectable length of therapy tape from the roll of therapy tape) and may be adhered to a patient's skin. In embodiments in which the adhesive layer of the therapy tape is heat activated by a patient's body heat after application of the tape to the patient.

Once the therapy tape is securely adhered to the patient's skin, a tensile force may be applied to one or more of the handles (e.g., by pulling one or more of the handles) to lift a portion of the patient's skin adjacent to the one or more handles. In various embodiments, the tensile force may be applied at least substantially normal to the surface of the patient's skin (e.g., at least substantially perpendicular to the patient's skin), however the tensile force may be applied at an acute angle relative to the patient's skin (e.g., between 0-90 degrees relative to the patient's skin). As just one non-limiting example, the tensile force may be applied at an angle between about 45-90 degrees relative to the patient's skin. The tensile force may be applied as a part of a multi-way skin and/or tissue massage and/or manipulation treatment. For example, the handles may be pulled and/or twisted and the tape may be compressed during the treatment. For example, the handles may be pulled in any direction (e.g., in a direction aligned at least in part with the length of the tape, in a direction aligned at least in part with the width of the tape, in a direction normal to the tape, and/or any directions in between). The one or more handles may also be twisted (e.g., around an axis normal to the tape, around an axis parallel with the length of the tape, around an axis parallel with the width of the tape, and/or any axis in between).

In embodiments comprising detachable handles and a connecting portion, the therapy tape may be applied as discussed above. Once applied to a patient's skin, one or more of the detachable handles may be secured relative to one or more connecting portions. Once secured, a tensile force may be applied to one or more of the detachable handles (e.g., by pulling one or more of the detachable handles) to lift the therapy tape and an adjacent portion of the patient's skin.

Moreover, in embodiments comprising one or more stimulators, the therapy tape comprising the one or more stimulators may be applied to a patient's skin. Once applied, the one or more stimulators may be activated by receiving an activation signal from the controller. In various embodiments, the controller may comprise a user interface disposed thereon (e.g., power switch, intensity selector, and/or the like), and accordingly the one or more stimulators may be activated by the controller in response to receipt of user input by the controller. Moreover, in certain embodiments, the controller may be in electronic communication (e.g., wired and/or wireless) with one or more external computing entities (e.g. handheld computing entities, user computing entities, and/or the like). In various embodiments, the one or more electronic computing entities may be configured to generate and transmit one or more electronic signals to the controller to cause the controller to activate or otherwise control the one or more stimulators. For example, a user may provide user input to the external computing entity indicative of a desired power level (e.g., vibration intensity, TENS signal intensity, pressure application intensity, and/or the like). In response to receipt of the user input, the external computing entity may transmit a signal to the controller of the therapy tape, causing the controller to generate and transmit corresponding signals to the one or more stimulators causing the stimulators to activate.

Moreover, as discussed herein, the therapy tape comprising the one or more stimulators may additionally comprise one or more handles (previously secured thereto and/or detachable). Accordingly, a tensile force may be applied to the one or more handles before, during, and/or after activating one or more stimulators embodied within the therapy tape.

CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

As discussed herein, the therapy tape may be usable with human patients (e.g., children, adolescents, adults, elderly, and/or the like). Certain embodiments may be usable with animal patients (e.g., horses, cats, dogs, and/or the like). Moreover, as discussed herein, various embodiments may be applied directly to a patient's skin. However, in various embodiments, therapy tape may be embedded within and/or on clothing (e.g., compression fit clothing, loose-fit clothing, smart clothing (e.g., having one or more network connected devices embedded therein), support devices (e.g., support sleeves, and/or the like), and/or the like.

That which is claimed:

1. A formed roll of therapy tape comprising:
   a continuous, elongated flexible backing layer having a top side and a bottom side opposite the top side;
   a continuous adhesive layer comprising a first adhesive material secured to the bottom side of the elongated flexible backing layer and covering an entirety of the bottom side of the elongated flexible backing layer;
   a plurality of handles comprising a first handle and a second handle spaced along a length of the flexible backing layer, wherein each of the plurality of handles comprises an elongated material secured onto the top side of the flexible backing layer and extends across at least a portion of a width of the flexible backing layer perpendicular to the length, and wherein each of the plurality of handles comprises:
      a base portion extending between a first end and a second end of the base portion along a length of the base portion, wherein the length of the base portion is at least substantially parallel to the length of the flexible backing layer, and wherein the base portion defines an area of the handle permanently secured onto the top side of the flexible backing layer via a second adhesive material, wherein the second adhesive material is configured to permanently secure the plurality of handles relative to the top side of the flexible backing layer; and a grip portion extending away from the base portion; and wherein a first end of the first handle is spaced a distance away from a second end of the second handle along the length of the flexible backing layer such that the first handle is discrete and separated from the second handle;

wherein the first adhesive material is configured to maintain adherence with the flexible backing layer and a patient's skin while at least one of the plurality of handles is pulled normal to the patient's skin; and wherein the elongated flexible backing material and the plurality of handles form the roll of therapy tape.

2. The formed roll of therapy tape of claim 1, wherein each of the plurality of handles comprises an inelastic material.

3. The formed roll of therapy tape of claim 2, wherein the flexible backing layer comprises an elastic material.

4. The formed roll of therapy tape of claim 1, wherein the grip portion of each of the plurality of handles is rigid.

5. The formed roll of therapy tape of claim 1, wherein the first adhesive material is configured to be heat activated by the patient's body heat.

6. The formed roll of therapy tape of claim 1, wherein the flexible backing layer is inelastic.

7. The formed roll of therapy tape of claim 5, wherein the base portion of each handle comprises one ply of flexible material.

8. The formed roll of therapy tape of claim 1, wherein at least one of the plurality of handles comprises a folded single-ply flexible sheet secured relative to the flexible backing layer.

9. The formed roll of therapy tape of claim 1, wherein the first adhesive material is secured to the backing layer such that the adhesive material and the backing layer are configured to not delaminate upon removal from the patient's skin.

10. The formed roll of therapy tape of claim 1, wherein the length of the flexible backing layer extends between a first end and a second end of the flexible backing layer, and wherein each of the plurality of handles are spaced a distance away from the first end and the second end of the flexible backing layer.

11. The formed roll of therapy tape of claim 1, wherein the grip portion of each of the plurality of handles comprises two plies of flexible material.

12. The formed roll of therapy tape of claim 1, wherein lengths of the elongated flexible backing material and the plurality of handles are configured to be detached from the formed roll of therapy tape.

* * * * *

UNITED STATES PATENT AND TRADEMARK OFFICE
CERTIFICATE OF CORRECTION

PATENT NO. : 11,096,817 B2
APPLICATION NO. : 15/297410
DATED : August 24, 2021
INVENTOR(S) : Hietanen et al.

It is certified that error appears in the above-identified patent and that said Letters Patent is hereby corrected as shown below:

In the Claims

Column 18,
Line 3, "claim 5" should read --claim 4--.

Signed and Sealed this
Thirty-first Day of May, 2022

Katherine Kelly Vidal
*Director of the United States Patent and Trademark Office*